United States Patent
Sakane

(10) Patent No.: US 9,777,135 B2
(45) Date of Patent: Oct. 3, 2017

(54) EPOXY-AMINE ADDUCT, RESIN COMPOSITION, SIZING AGENT, CARBON FIBER COATED WITH SIZING AGENT, AND FIBER-REINFORCED COMPOSITE MATERIAL

(71) Applicant: DAICEL CORPORATION, Osaka-shi, Osaka (JP)

(72) Inventor: Masanori Sakane, Ohtake (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

(21) Appl. No.: 15/191,041

(22) Filed: Jun. 23, 2016

(65) Prior Publication Data

US 2016/0369087 A1    Dec. 22, 2016

Related U.S. Application Data

(62) Division of application No. 14/401,477, filed as application No. PCT/JP2013/062601 on Apr. 30, 2013, now Pat. No. 9,388,294.

(30) Foreign Application Priority Data

May 16, 2012  (JP) ................. 2012-112148
Aug. 23, 2012 (JP) ................. 2012-183942

(51) Int. Cl.
| | | |
|---|---|---|
| B32B 27/04 | (2006.01) | |
| B32B 27/18 | (2006.01) | |
| D06M 15/61 | (2006.01) | |
| C08L 79/02 | (2006.01) | |
| C08G 59/00 | (2006.01) | |
| C08K 5/17 | (2006.01) | |
| C08G 59/18 | (2006.01) | |
| C08G 59/24 | (2006.01) | |
| C07D 303/36 | (2006.01) | |
| C08J 5/06 | (2006.01) | |
| C08J 5/24 | (2006.01) | |
| C07C 215/44 | (2006.01) | |
| C08G 59/14 | (2006.01) | |

(52) U.S. Cl.
CPC .............. *C08K 5/17* (2013.01); *C07C 215/44* (2013.01); *C07D 303/36* (2013.01); *C08G 59/1477* (2013.01); *C08G 59/184* (2013.01); *C08G 59/24* (2013.01); *C08J 5/06* (2013.01); *C08J 5/24* (2013.01); *C07C 2601/14* (2017.05); *C08J 2363/02* (2013.01); *Y10T 428/2918* (2015.01)

(58) Field of Classification Search
None
See application file for complete search history.

(56) References Cited

U.S. PATENT DOCUMENTS

| 3,625,918 A | 12/1971 | Heer et al. |
|---|---|---|
| 4,686,250 A | 8/1987 | Qureshi |
| 9,388,294 B2 * | 7/2016 | Sakane .............. C08G 59/184 |
| 2003/0135011 A1 | 7/2003 | Goto et al. |
| 2015/0152259 A1 | 6/2015 | Sakane |

FOREIGN PATENT DOCUMENTS

| EP | 0 228 277 A2 | 7/1987 |
|---|---|---|
| EP | 0 228 277 A3 | 7/1987 |
| EP | 0 822 953 A1 | 2/1998 |
| GB | 980268 A | 1/1966 |
| JP | 47-39396 A | 12/1972 |
| JP | 50-59589 A | 5/1975 |
| JP | 56-155222 A | 12/1981 |
| JP | 57-100127 A | 6/1982 |
| JP | 57-128266 A | 8/1982 |
| JP | 57-171767 A | 10/1982 |
| JP | 59-9273 A | 1/1984 |
| JP | 61-28074 A | 2/1986 |
| JP | 61-228018 A | 10/1986 |
| JP | 62-33872 A | 2/1987 |
| JP | 62-164715 A | 7/1987 |
| JP | 1-272867 A | 10/1989 |
| JP | 7-9444 A | 1/1995 |

(Continued)

OTHER PUBLICATIONS

Machine translation of JP 2012-097383 (no date).*
International Search Report, dated May 28, 2013, issued in PCT/JP2013/062598.
International Search Report, dated May 28, 2013, issued in PCT/JP2013/062601.
U.S. Office Action, dated Jul. 6, 2015, issued in U.S. Appl. No. 14/401,447.
U.S. Office Action, dated Jun. 23, 2015 in U.S. Appl. No. 14/401,477.

*Primary Examiner* — Michael J Feely
(74) *Attorney, Agent, or Firm* — Birch, Stewart, Kolasch & Birch, LLP

(57) ABSTRACT

Provided is an epoxy-amine adduct that offers high reactivity, contributes to better adhesion between a resin and a reinforcing fiber in a fiber-reinforced composite material, and can be easily blended with another component such as a resin. The epoxy-amine adduct has two or more amino groups per molecule and is obtained by a reaction of an epoxy compound (A) having two or more alicyclic epoxy groups per molecule with an amine compound (B) having two or more amino groups per molecule. The epoxy compound (A) is preferably a compound represented by Formula (a):

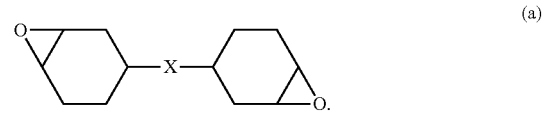

9 Claims, 4 Drawing Sheets

(56) References Cited

FOREIGN PATENT DOCUMENTS

| | | |
|---|---|---|
| JP | 11-504061 A | 4/1999 |
| JP | 2000-336577 A | 12/2000 |
| JP | 2012-77426 A | 4/2012 |
| JP | 2012-097383 A | 5/2012 |
| WO | WO 96/34032 A1 | 10/1996 |

* cited by examiner

EPOXY-AMINE ADDUCT, RESIN COMPOSITION, SIZING AGENT, CARBON FIBER COATED WITH SIZING AGENT, AND FIBER-REINFORCED COMPOSITE MATERIAL

This application is a Divisional of copending application Ser. No. 14/401,477, filed on Nov. 14, 2014, which was filed as PCT International Application No. PCT/JP2013/062601 on Apr. 30, 2013, which claims the benefit under 35 U.S.C. §119(a) to Patent Application No. 2012-112148, filed in Japan on May 16, 2012, and Patent Application No. 2012-183942, filed in Japan on Aug. 23, 2012, all of which are hereby expressly incorporated by reference into the present application.

TECHNICAL FIELD

The present invention relates to an epoxy-amine adduct; a resin composition including the epoxy-amine adduct; and a fiber-reinforced composite material formed from a prepreg that is obtained by impregnating or coating a reinforcing fiber with the resin composition. The present invention further relates to a sizing agent including the epoxy-amine adduct; a sizing-agent-coated carbon fiber obtained by applying the sizing agent to a carbon fiber; and a fiber-reinforced composite material including the sizing-agent-coated carbon fiber.

BACKGROUND ART

There have been known epoxy-amine adducts formed by a reaction between an amine compound and an epoxy compound. Such epoxy-amine adducts are also called "amine adducts." As examples of the amine adducts, Patent Literature (PTL) 1 and PTL 2 disclose addition compounds each obtained by allowing a glycidyl-containing epoxy resin to react with a dialkylamine; and powders of the addition compounds whose surface is neutralized with an acidic substance. PTL 3 discloses an epoxy-amine adduct that is obtained by a reaction typically of an amino compound having an amino group and an N,N-dialkylamino group with an epoxy resin having more than one glycidyl group on average per molecule in a specific ratio.

The amine adducts are used as curing agents (latent curing agents) for epoxy resins, as disclosed in PTL 1 to 3. In addition to the curing agent use, the amine adducts have recently been used typically as adhesion improvers that are used in composite materials (fiber-reinforced composite materials) including a reinforcing fiber and a resin for better adhesion between the resin and the reinforcing fiber. The reinforcing fiber is exemplified by carbon fibers.

Separately, carbon-fiber-reinforced composite materials have very excellent heat resistance and mechanical properties and have been increasingly used in various uses. The carbon-fiber-reinforced composite materials are fiber-reinforced composite materials as composite materials of a carbon fiber and a resin, where the carbon fiber has a specific strength, a specific modulus, and heat resistance at high levels and is lightweight. The carbon-fiber composite materials generally employ sizing agents (binders). The sizing agents are exemplified by bisphenol-A diglycidyl ether (see PTL 4 and 5), poly(alkylene oxide) adducts of bisphenol-A (see PTL 6 and 7), poly(alkylene oxide) adducts of bisphenol-A to which epoxy group is added (see PTL 8 and 9), and epoxy adducts of polyalkylene glycols (see PTL 10 to 12). The sizing agents are applied as a paste or sizing material to a carbon fiber so as to improve workability in higher-order processing of the carbon fiber that has poor compactness.

CITATION LIST

Patent Literature

PTL 1: Japanese Unexamined Patent Application Publication (JP-A) No. S56-155222
PTL 2: JP-A No. S57-100127
PTL 3: JP-A No. S61-228018
PTL 4: JP-A No. S50-059589
PTL 5: JP-A No. S57-171767
PTL 6: JP-A No. H07-009444
PTL 7: JP-A No. 2000-336577
PTL 8: JP-A No. S61-028074
PTL 9: JP-A No. H01-272867
PTL 10: JP-A No. S57-128266
PTL 11: JP-A No. S59-009273
PTL 12: JP-A No. S62-033872

SUMMARY OF INVENTION

Technical Problem

Unfortunately, the amine adducts disclosed in PTL 1 to 3 fail to have sufficient reactivity because they have no active hydrogen such as hydrogen atom directly bonded to a nitrogen atom or, even when having the active hydrogen, the active hydrogen is masked by a compound of various types (such as an inorganic acid, an organic acid, or a phenol). The amine adducts thereby fail to sufficiently effectively contribute to better adhesion between the resin and the reinforcing fiber when used typically as adhesion improvers in the fiber-reinforced composite materials.

When designed to be used as additives typically for improving adhesion between a resin and a reinforcing fiber in fiber-reinforced composite materials, amine adducts should be capable of being easily blended with another component such as a thermoplastic resin or a curable resin (e.g., an epoxy resin). However, the customarily known adducts of bisphenol-A diglycidyl ether or another glycidyl-containing epoxy compound with a polyamine compound have a crosslinked structure as formed, thereby resist softening or melting even upon heating, are hardly blended with another component, and fail to give homogeneous compositions.

In addition, demands have been made to provide sizing agents for use in the carbon-fiber-reinforced composite materials, which sizing agents can contribute to not only better workability in higher-order processing of the carbon fiber, but also better adhesiveness (adhesion) between the carbon fiber and the resin (matrix resin) in the carbon-fiber-reinforced composite materials.

Accordingly, an object of the present invention is to provide an epoxy-amine adduct that offers high reactivity, helps a fiber-reinforced composite material to include a resin and a reinforcing fiber with better adhesion to each other, and can be easily blended with another component such as the resin.

Another object of the present invention is to provide a resin composition that offers high reactivity and can form a fiber-reinforced composite material including a resin and a reinforcing fiber adhered to each other excellently.

Yet another object of the present invention is to provide a fiber-reinforced composite material that includes a resin and a reinforcing fiber adhered to each other excellently and offers high-level mechanical properties such as toughness.

Still another object of the present invention is to provide a sizing agent that can help a carbon fiber to have better workability in higher-order processing and to have better adhesiveness with a matrix resin.

Another object of the present invention is to provide a sizing-agent-coated carbon fiber; and a fiber-reinforced composite material including the sizing-agent-coated carbon fiber, where the sizing-agent-coated carbon fiber has excellent workability in higher-order processing and includes a carbon fiber and a matrix resin adhered to each other excellently.

Solution to Problem

After intensive investigations to achieve the objects, the present inventor has found that an epoxy-amine adduct (amine adduct) obtained by a reaction between a specific epoxy compound and a specific amine compound, or an epoxy-amine adduct (amine adduct) having a specific structure offers high reactivity and, when used in a fiber-reinforced composite material including a resin and a reinforcing fiber, can help the resin and the reinforcing fiber to have better adhesion between them, and can be easily blended with another component such as the resin. The present invention has been made based on these findings.

Specifically, the present invention provides an epoxy-amine adduct that has two or more amino groups per molecule and is obtained by a reaction of an epoxy compound (A) having two or more alicyclic epoxy groups per molecule with an amine compound (B) having two or more amino groups per molecule.

The epoxy compound (A) may be a compound represented by Formula (a):

[Chem. 1]

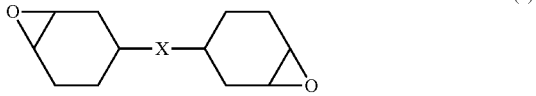
(a)

where X is selected from a single bond and a divalent group having at least one atom.

The amine compound (B) may be a compound represented by Formula (b):
[Chem. 2]

(b)

where $R^2$ represents an organic group having a valency of r and having a carbon atom at each bonding site with the nitrogen atom specified in the formula; and r represents an integer of 2 or more.

The present invention further provides an epoxy-amine adduct represented by Formula (I):

[Chem. 3]

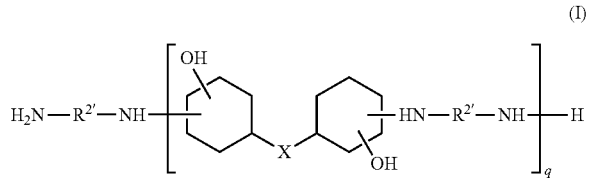
(I)

where $R^{2'}$ represents a divalent organic group having a carbon atom at each bonding site with the nitrogen atom specified in the formula; X is, in each occurrence independently, selected from a single bond and a divalent group having at least one atom; and q represents an integer of 1 or more.

The present invention further provides a resin composition including the epoxy-amine adduct and a thermoplastic resin.

The resin composition may be used as a resin composition for a fiber-reinforced composite material.

The present invention further provides a prepreg including the resin composition; and a reinforcing fiber impregnated or coated with the resin composition.

The present invention further provide a fiber-reinforced composite material formed from the prepreg.

The present invention also provides a sizing agent including the epoxy-amine adduct.

The present invention further provides a sizing-agent-coated carbon fiber including the sizing agent; and a carbon fiber coated with the sizing agent.

In addition and advantageously, the present invention provides a fiber-reinforced composite material including the sizing-agent-coated carbon fiber; and one selected from a thermoplastic resin and a cured product of a curable compound.

Advantageous Effects of Invention

The epoxy-amine adduct according to the present invention, as having the configuration, offers high reactivity with a functional group (such as hydroxyl, carboxyl, or epoxy group) present in the surface of the reinforcing fiber and can effectively help a fiber-reinforced composite material to include a resin and a reinforcing fiber adhered to each other excellently. In addition, the epoxy-amine adduct according to the present invention can be softened or melted at least by heating or is satisfactorily soluble typically in a solvent and/or a resin, and can thereby be easily blended with another component. The epoxy-amine adduct according to the present invention upon use can therefore give a resin composition capable of forming a fiber-reinforced composite material including a resin and a reinforcing fiber adhered to each other excellently. In addition, the epoxy-amine adduct can give a fiber-reinforced composite material that includes a resin and a reinforcing fiber adhered to each other excellently and offers satisfactory mechanical properties (particularly, toughness).

The sizing agent according to the present invention, as having the configuration, can help a carbon fiber to have better workability in higher-order processing and to have better adhesiveness with a matrix resin. A sizing-agent-coated carbon fiber obtained by coating a carbon fiber with the sizing agent according to the present invention therefore has excellent workability in higher-order processing and offers excellent adhesion of the carbon fiber with a matrix resin. In addition, a fiber-reinforced composite material including the sizing-agent-coated carbon fiber has excellent heat resistance and mechanical strengths and is obtained with high productivity.

DESCRIPTION OF EMBODIMENTS

Epoxy-amine Adduct

Figure 1:
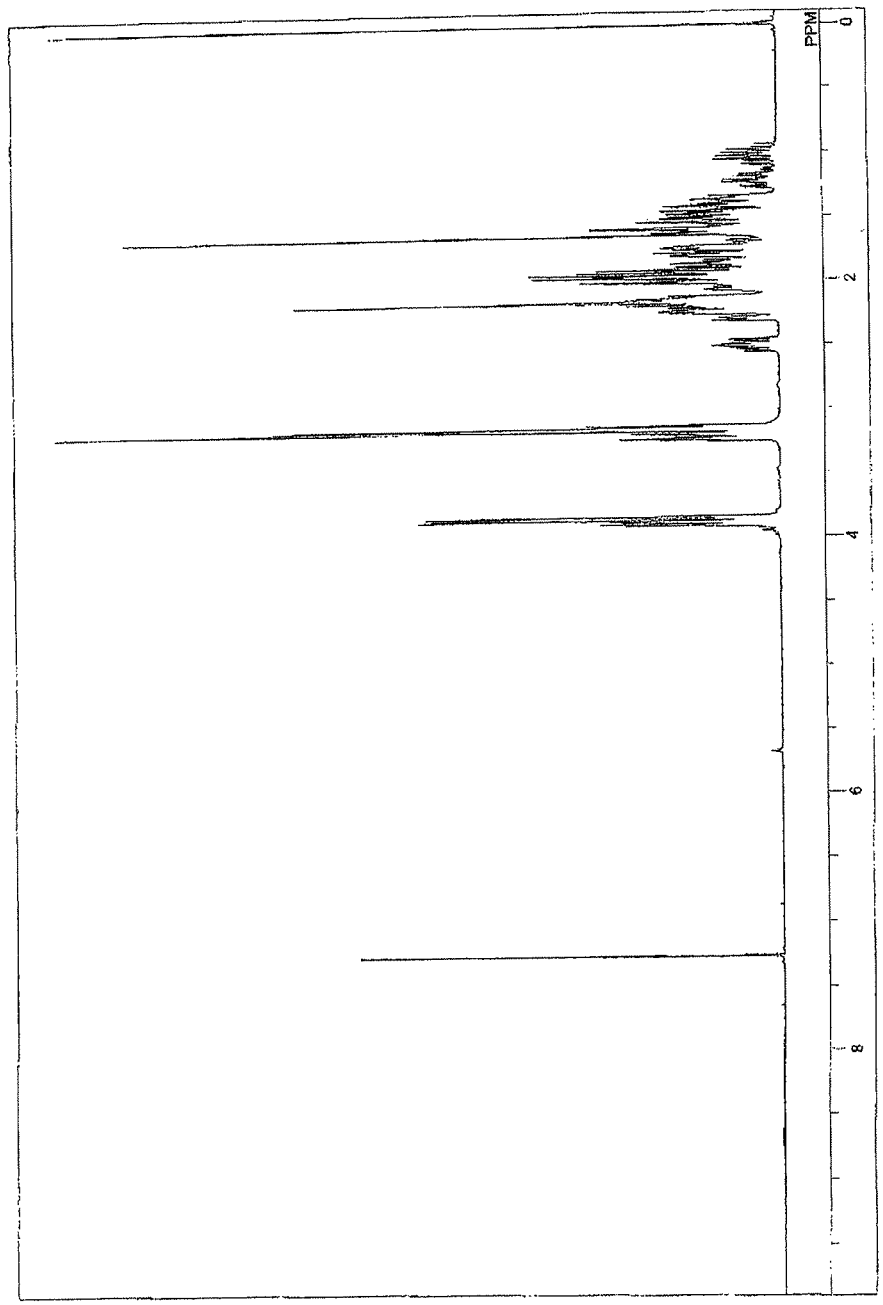
FIG. 1 depicts a $^1$H-NMR spectrum chart of an epoxy compound (CELLOXIDE 2021P) used as a raw material in examples.
Figure 2:
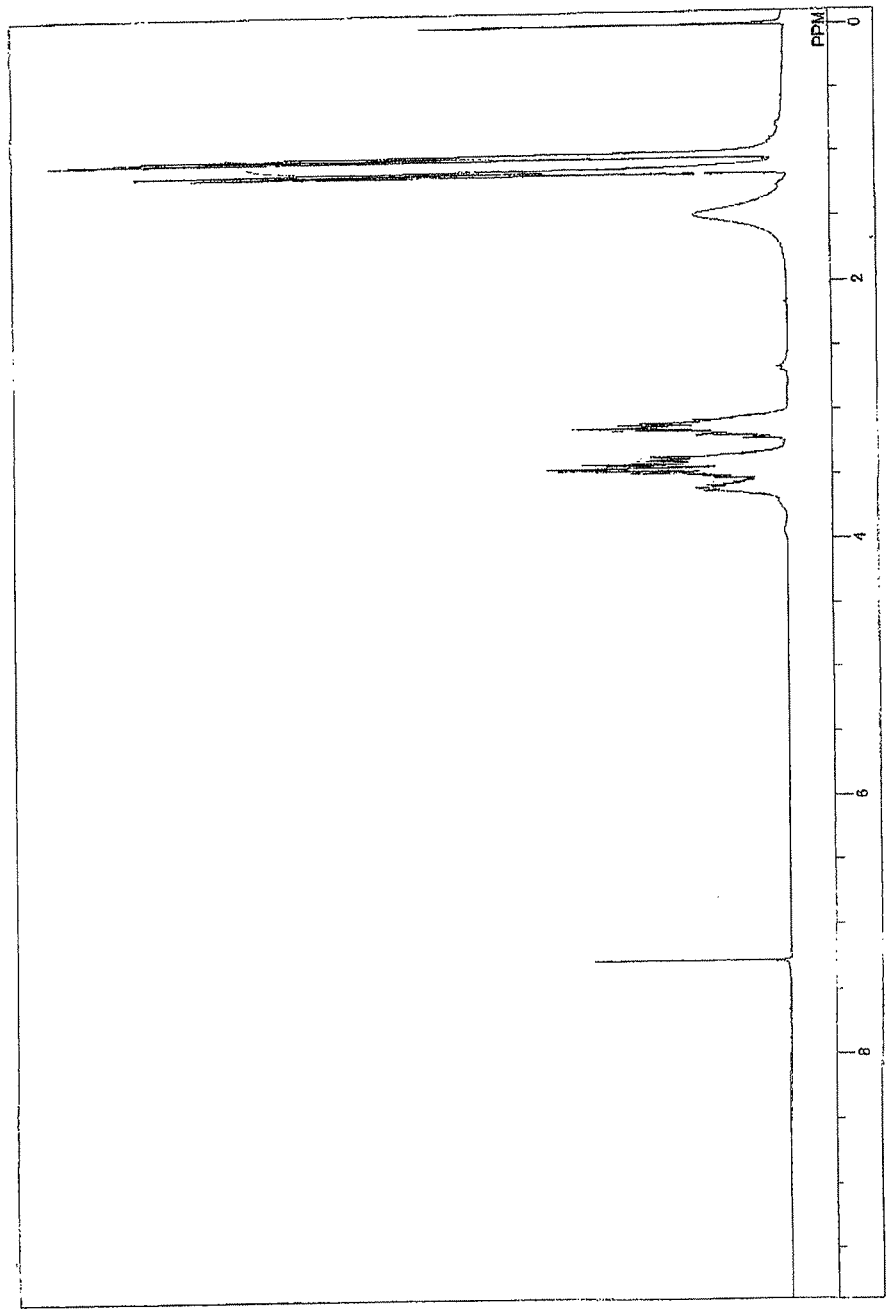
FIG. 2 depicts a ¹H-NMR spectrum chart of an amine compound (JEFFAMINE D-230) used as a raw material in the examples.

The epoxy-amine adduct according to an embodiment of the present invention is an epoxy-amine adduct that has two or more amino groups per molecule and is obtained by a reaction of an epoxy compound (A) with an amine compound (B). The "epoxy compound (A)" refers to an epoxy compound having two or more alicyclic epoxy groups per molecule; whereas the "amine compound (B)" refers to an amine compound having two or more amino groups per molecule. More specifically, the epoxy-amine adduct according to the present invention is an epoxy-amine adduct having two or more amino groups per molecule and obtained by a reaction between alicyclic epoxy groups of the epoxy compound (A) and amino groups of the amine compound (B). As used herein the term "amino group" refers to $-NH_2$ (unsubstituted amino group) unless otherwise specified; and the term "—NH— group" does not include the unsubstituted amino group ($-NH_2$).

Epoxy Compound (A)

The epoxy compound (A) serving as a raw material (precursor) to form the epoxy-amine adduct according to the present invention is a polyepoxy compound (alicyclic epoxy compound) having two or more alicyclic epoxy groups per molecule. As used herein the term "alicyclic epoxy group" refers to an epoxy group that is formed by an oxygen atom and adjacent two carbon atoms constituting an alicycle (aliphatic ring).

The alicyclic epoxy groups of the epoxy compound (A) are exemplified by, but not limited to, epoxy groups each composed of an oxygen atom and adjacent two carbon atoms constituting a $C_4$-$C_{16}$ aliphatic ring (aliphatic hydrocarbon ring), such as cyclobutane, cyclopentane, cyclohexane, or cycloheptane ring. Among them, epoxy groups (cyclohexene oxide groups) composed of an oxygen atom and two carbon atoms constituting a cyclohexane ring are preferred as the alicyclic epoxy groups.

The epoxy compound (A) may have the alicyclic epoxy groups in a number per molecule not critical, as long as being 2 or more, but preferably from 2 to 6, more preferably from 2 to 5, and furthermore preferably 2 or 3. The epoxy compound (A), if having alicyclic epoxy groups in a number greater than 6, may cause the epoxy-amine adduct formed by a reaction with the amine compound (B) to be hardly blended with another component.

As the epoxy compound (A), particularly preferred are compounds (epoxy compounds) represented by Formula (a):

[Chem. 4]

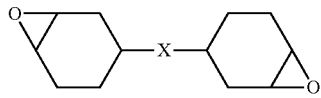

(a)

X in Formula (a) is selected from a single bond and a linkage group (divalent group having at least one atom). The linkage group is exemplified by divalent hydrocarbon groups, carbonyl group, ether bond, ester bond, carbonate group, amido group, and groups each including two or more of these groups linked to each other.

The epoxy compound (A) of Formula (a), when X is a single bond, is 3,4,3',4'-diepoxybicyclohexane.

The divalent hydrocarbon groups are exemplified by $C_1$-$C_{18}$ linear or branched chain alkylene groups; and divalent alicyclic hydrocarbon groups. The $C_1$-$C_{18}$ linear or branched chain alkylene groups are exemplified by methylene, methylmethylene, dimethylmethylene, ethylene, propylene, and trimethylene groups. The divalent alicyclic hydrocarbon groups are exemplified by divalent cycloalkylene groups (including cycloalkylidene groups) such as 1,2-cyclopentylene, 1,3-cyclopentylene, cyclopentylidene, 1,2-cyclohexylene, 1,3-cyclohexylene, 1,4-cyclohexylene, and cyclohexylidene groups.

Among them, the linkage group X is preferably an oxygen-containing linkage group which is specifically exemplified by —CO—, —O—CO—O—, —CO—O—, —O—, and —CO—NH—; a group including two or more of these groups linked to each other; and a group including one or more of these groups linked to one or more of divalent hydrocarbon groups. The divalent hydrocarbon groups are as exemplified above.

Typical examples of the alicyclic epoxy compounds represented by Formula (a) include compounds represented by Formulae (a-1) to (a-10) indicated below. In Formulae (a-5) and (a-7), l and m independently represent an integer from 1 to 30. In Formula (a-5), $R^1$ represents a $C_1$-$C_8$ alkylene group, which is exemplified by linear or branched chain alkylene groups such as methylene, ethylene, propylene, isopropylene, butylene, isobutylene, s-butylene, pentylene, hexylene, heptylene, and octylene groups. Among them, preferred are $C_1$-$C_3$ linear or branched chain alkylene groups, such as methylene, ethylene, propylene, and isopropylene groups. In Formulae (a-9) and (a-10), n1, n2, n3, n4, n5, and n6 independently represent an integer of from 1 to 30.

[Chem. 5]

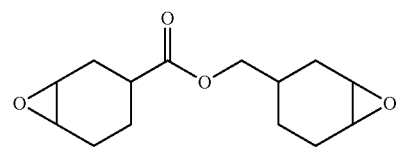

(a-1)

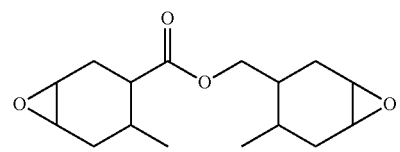

(a-2)

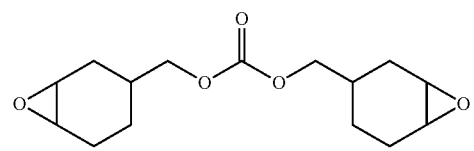

(a-3)

-continued

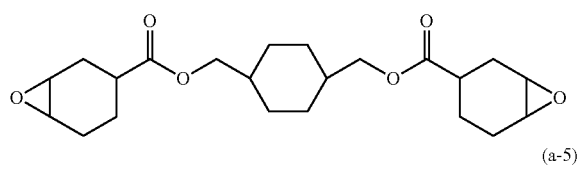
(a-4)

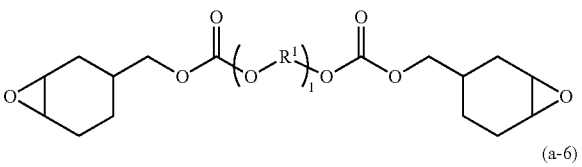
(a-5)

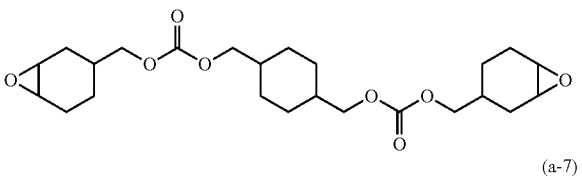
(a-6)

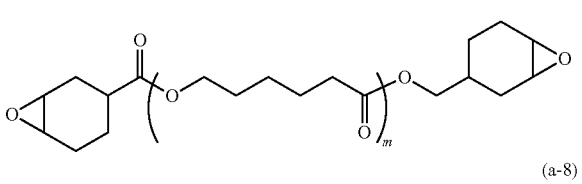
(a-7)

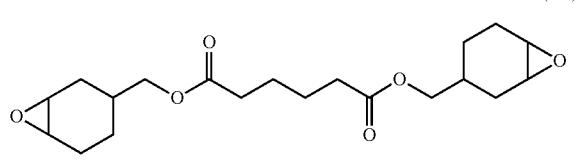
(a-8)

[Chem. 6]

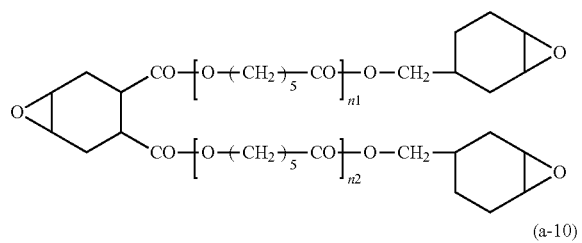
(a-9)

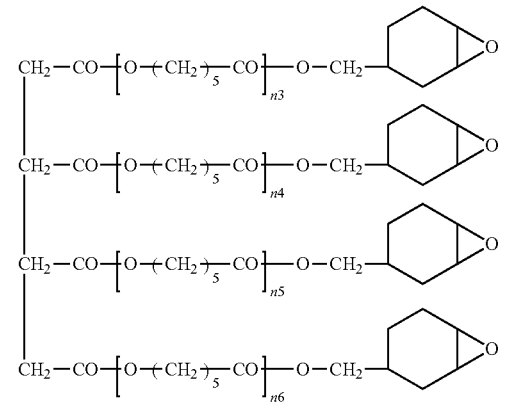
(a-10)

Of the compounds represented by Formula (a), preferred is the compound represented by Formula (a-1) [3,4-epoxy-cyclohexylmethyl (3,4-epoxy)cyclohexanecarboxylate; available typically under the trade name of CELLOXIDE 2021P (from Daicel Corporation)]. The compound is preferred from the viewpoints of heat resistance and handleability.

Amine Compound (B)

The amine compound (B) serving as a raw material (precursor) to form the epoxy-amine adduct according to the present invention is a polyamine compound having two or more amino groups (—$NH_2$; unsubstituted amino groups) per molecule. The amine compound (B) may have amino groups in a number per molecule not critical, as long as being 2 or more, but preferably from 2 to 6, more preferably from 2 to 5, and furthermore preferably 2 or 3. The amine compound (B), if having amino groups in a number greater than 6, may cause the epoxy-amine adduct formed by a reaction with the epoxy compound (A) to be hardly blended with another component.

The amine compound (B) may have a molecular weight not critical, but preferably from 80 to 10000, more preferably from 100 to 5000, and furthermore preferably from 200 to 1000. The amine compound (B), if having a molecular weight less than 80, may cause the epoxy-amine adduct to include an excessively large amount of after-mentioned —NH— groups (substituted amino groups) and may cause a cured product (cured resin) to be excessively brittle, which cured product is obtained by blending the epoxy-amine adduct with a curable resin (curable compound) to give a composition and curing the composition. In contrast, the amine compound (B), if having a molecular weight of more than 10000, may less effectively allow the epoxy compound (A) to react therewith. In addition or alternatively, this amine compound (B) may fail to help the epoxy-amine adduct to sufficiently effectively function upon incorporation. Typically, the epoxy-amine adduct in this case may fail to sufficiently contribute to better heat resistance of the cured product (cured resin) and to better heat resistance and toughness of the fiber-reinforced composite material.

The amine compound (B) is exemplified by amine compounds having a valency of r and represented by Formula (b):

[Chem. 7]

$$R^2(NH_2)_r \quad (b)$$

In Formula (b), r represents an integer of 2 or more. The number r is not critical, as long as being an integer of 2 or more, but preferably from 2 to 6, more preferably from 2 to 5, and furthermore preferably 2 or 3.

$R^2$ in Formula (b) represents an organic group (organic residue) having a valency of r and having a carbon atom at each bonding site with the nitrogen atom specified in the formula. $R^2$ is exemplified by r-valent linear or branched chain aliphatic hydrocarbon groups; r-valent cyclic aliphatic hydrocarbon groups; r-valent aromatic hydrocarbon groups; and r-valent groups each including two or more of these groups bonded directly or through a heteroatom-containing linkage group (divalent group).

The r-valent linear or branched chain aliphatic hydrocarbon groups are exemplified by divalent linear or branched chain aliphatic hydrocarbon groups, trivalent linear or branched chain aliphatic hydrocarbon groups, and tetravalent linear or branched chain aliphatic hydrocarbon groups. The divalent linear or branched chain aliphatic hydrocarbon groups are exemplified by alkylene and alykenylene groups. The alkylene groups are exemplified by $C_1$-$C_{30}$ linear or branched chain alkylene groups, such as methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, and octadecylene groups; of which $C_1$-$C_{18}$ alkylene groups are preferred. The alkenylene groups are exemplified by alkenylene groups corresponding to the alkylene groups, including $C_2$-$C_{30}$ linear or branched chain alkenylene groups, such as vinylene and allylene groups; of which $C_2$-$C_{18}$ alkenylene groups are more preferred. The trivalent linear or branched chain aliphatic hydrocarbon groups are exemplified by alkane-triyl groups including $C_3$-$C_{30}$ linear or branched chain alkane-triyl groups, such as propane-triyl and 1,1,1-trimethylpropane-triyl groups; of which $C_3$-$C_{18}$ alkane-triyl groups are preferred. The tetravalent linear or branched chain aliphatic hydrocarbon groups are exemplified by alkane-tetrayl groups including $C_4$-$C_{30}$ linear or branched chain alkane-tetrayl groups, such as butane-tetrayl and 2,2-dimethylpropane-tetrayl groups; of which $C_4$-$C_{18}$ alkane-tetrayl groups are preferred.

The r-valent linear or branched chain aliphatic hydrocarbon groups may each have one or more substituents. Namely, at least one of hydrogen atoms of each r-valent linear or branched chain aliphatic hydrocarbon group may be substituted with a variety of substituent. The substituents are exemplified by halogen, oxo, hydroxyl, substituted oxy (e.g., alkoxy, aryloxy, aralkyloxy, and acyloxy), carboxyl, substituted oxycarbonyl (e.g., alkoxycarbonyl, aryloxycarbonyl, and aralkyloxycarbonyl), substituted or unsubstituted carbamoyl, cyano, nitro, substituted or unsubstituted amino, sulfo, and heterocyclic groups. The hydroxyl and carboxyl groups may each be protected by a protecting group commonly used in organic syntheses. The protecting group is exemplified by acyl, alkoxycarbonyl, organic silyl, alkoxyalkyl, and oxacycloalkyl groups.

The substituted or unsubstituted carbamoyl groups are exemplified by carbamoyl groups each having, for example, an alkyl group or an acyl group; and unsubstituted carbamoyl group, where alkyl group is exemplified by methyl, ethyl, propyl, isopropyl, n-butyl, s-butyl, and t-butyl groups, and the acyl group is exemplified by acetyl and benzoyl groups. The substituted or unsubstituted amino groups are exemplified by amino groups having an alkyl group or an acyl group; and unsubstituted amino group, in which the alkyl group is exemplified by methyl, ethyl, propyl, isopropyl, n-butyl, s-butyl, and t-butyl groups; and the acyl group is exemplified by acetyl and benzoyl groups.

Heterocyclic rings constituting the heterocyclic groups include aromatic heterocyclic rings and non-aromatic heterocyclic rings. Such heterocyclic rings are exemplified by heterocyclic rings containing oxygen as a heteroatom (oxygen-containing heterocyclic rings); heterocyclic rings containing sulfur as a heteroatom (sulfur-containing heterocyclic rings); and heterocyclic rings containing nitrogen as a heteroatom (nitrogen-containing heterocyclic rings). The oxygen-containing heterocyclic rings are exemplified by three-membered rings such as oxirane ring; four-membered rings such as oxetane ring; five-membered rings such as furan, tetrahydrofuran, oxazole, and γ-butyrolactone rings; six-membered rings such as 4-oxo-4H-pyran, tetrahydropyran, and morpholine rings; fused rings such as benzofuran, 4-oxo-4H-chromene, and chromane rings; and bridged rings such as 3-oxatricyclo[4.3.1.1$^{4,8}$]undecan-2-one and 3-oxatricyclo[4.2.1.0$^{4,8}$]nonan-2-one rings. The sulfur-containing heterocyclic rings are exemplified by five-membered rings such as thiophene, triazole, and thiadiazole rings; six-membered rings such as 4-oxo-4H-thiopyran ring; and fused rings such as benzothiophene ring. The nitrogen-containing heterocyclic rings are exemplified by five-membered rings such as pyrrole, pyrrolidine, pyrazole, imidazole, and triazole rings; six-membered rings such as pyridine, pyridazine, pyrimidine, pyrazine, piperidine, and piperazine rings; and fused rings such as indole, indoline, quinoline, acridine, naphthyridine, quinazoline, and purine rings. The heterocyclic groups may each have one or more substituents. The substituents are exemplified by the substituents which the r-valent linear or branched chain aliphatic hydrocarbon groups may have; as well as alkyl groups including $C_{1-4}$ alkyl groups such as methyl and ethyl groups; cycloalkyl groups; and aryl groups such as phenyl and naphthyl groups. The nitrogen atom(s) constituting the heterocyclic rings may each be protected by a customary protecting group. The protecting group is exemplified by alkoxy, alkoxycarbonyl, alkenyloxycarbonyl, aralkyloxycarbonyl, aralkyl, acyl, arylsulfonyl, and alkylsulfonyl groups.

The r-valent cyclic aliphatic hydrocarbon groups are exemplified by divalent cyclic aliphatic hydrocarbon groups, trivalent cyclic aliphatic hydrocarbon groups, and tetravalent cyclic aliphatic hydrocarbon groups. The divalent cyclic aliphatic hydrocarbon groups are exemplified by cycloalkylene, cycloalkenylene, cycloalkylidene, cycloalkadienylene, and divalent polycyclic hydrocarbon groups. The cycloalkylene groups are exemplified by $C_3$-$C_{20}$ cycloalkylene groups such as cyclopropylene, cyclobutylene, cyclopentylene, and cyclohexylene groups; of which $C_3$-$C_{15}$ cycloalkylene groups are preferred. The cycloalkenylene groups are exemplified by cycloalkenylene groups corresponding to the cycloalkylene groups, including $C_3$-$C_{20}$ cycloalkenylene groups such as cyclohexenylene group; of which $C_3$-$C_{15}$ cycloalkenylene groups are preferred. The cycloalkylidene groups are exemplified by cycloalkylidene groups corresponding to the cycloalkylene groups, including $C_3$-$C_{20}$ cycloalkylidene groups such as cyclopentylidene and cyclohexylidene groups; of which $C_3$-$C_{15}$ cycloalkylidene groups are preferred. The cycloalkadienylene groups are exemplified by cycloalkadienylene groups corresponding to the cycloalkylene groups, including $C_4$-$C_{20}$ cycloalkadienylene groups such as cyclopentadienylene group; of which $C_4$-$C_{15}$ cycloalkadienylene groups are preferred. The divalent polycyclic hydrocarbon groups are exemplified by divalent spiro hydrocarbon groups, including diyl groups corresponding to Spiro hydrocarbons such as spiro[4.4]nonane and spiro[4.5]decane; divalent groups corresponding to hydrocarbon ring assemblies, such as diyl groups corresponding to hydrocarbon ring assemblies such as bicyclopropyl; and divalent bridged hydrocarbon groups, including diyl groups corresponding to bridged hydrocarbons such as bicyclo[2.1.0]pentane, bicyclo[3.2.1]octane, norbornane, norbornene, and adamantane. The trivalent cyclic aliphatic hydrocarbon groups are exemplified by cycloalkane-triyl groups and polycyclic hydrocarbon-triyl groups. The tetravalent cyclic aliphatic hydrocarbon groups are exemplified by cycloalkane-tetrayl groups and polycyclic hydrocarbon-tetrayl groups. The r-valent cyclic aliphatic hydrocarbon groups may each have one or more substitutes. The substituents are exemplified by the substituents which the r-valent linear or branched chain aliphatic hydrocarbon groups may have.

The r-valent aromatic hydrocarbon groups are exemplified by groups corresponding to aromatic hydrocarbons, except for removing hydrogen atom(s) in a number of r therefrom. The aromatic hydrocarbons are exemplified by benzene, naphthalene, anthracene, 9-phenylanthracene, 9,10-diphenylanthracene, naphthacene, pyrene, perylene, biphenyl, binaphthyl, and bianthryl. The r-valent aromatic hydrocarbon groups may each have one or more substituents. The substituents are exemplified by the substituents which the r-valent linear or branched chain aliphatic hydrocarbon groups may have.

The heteroatom-containing linkage group (divalent group) is exemplified by divalent groups each containing one or more heteroatoms (e.g., oxygen, nitrogen, and sulfur atoms), such as —CO— (carbonyl group), —O— (ether bond), —CO—O— (ester bond), —O—CO—O— (carbonate group), —CO—NH— (amido group), —CO—NR$^a$— (substituted amido group; where R$^a$ represents an alkyl group), —NH—, —NR$^b$— (where R$^b$ represents an alkyl group), —SO—, and —SO$_2$—; and divalent groups each including two or more of them linked to each other.

As the amine compound (B), preferred is a compound (polyetheramine) represented by Formula (b-1):
[Chem. 8]

(b-1)

In Formula (b-1), R$^3$ is selected from a divalent linear, branched chain, or cyclic aliphatic hydrocarbon group and a divalent group including one or more linear or branched chain aliphatic hydrocarbon groups and one or more cyclic aliphatic hydrocarbon groups linked to each other. The divalent linear, branched chain, or cyclic aliphatic hydrocarbon group is exemplified by the divalent linear, branched chain, or cyclic aliphatic hydrocarbon groups exemplified as R$^2$. The divalent linear, branched chain, or cyclic aliphatic hydrocarbon group as R$^3$ may have one or more substituents. The substituents are exemplified by the substituents which the r-valent linear or branched chain aliphatic hydrocarbon group may have.

Among them, R$^3$ is preferably a divalent linear or branched chain aliphatic hydrocarbon group, more preferably a $C_2$-$C_6$ linear or branched chain alkylene group, furthermore preferably a $C_2$-$C_4$ linear or branched chain alkylene group, and particularly preferably ethylene, trimethylene, or propylene group.

R$^4$ in Formula (b-1) is, in each occurrence independently, selected from a divalent linear, branched chain, or cyclic aliphatic hydrocarbon group; and a divalent group including one or more linear or branched chain aliphatic hydrocarbon groups and one or more cyclic aliphatic hydrocarbon groups linked to each other. The divalent linear, branched chain, or cyclic aliphatic hydrocarbon group is exemplified by the divalent linear, branched chain, or cyclic aliphatic hydrocarbon groups exemplified as R$^2$. The divalent linear, branched chain, or cyclic aliphatic hydrocarbon group as R$^4$ may have one or more substituents. Such substituents are exemplified by the substituents which the r-valent linear or branched chain aliphatic hydrocarbon groups may have.

Among them, R$^4$ is, in each occurrence independently, preferably a divalent linear or branched chain aliphatic hydrocarbon group, more preferably a $C_2$-$C_6$ linear or branched chain alkylene group, furthermore preferably a $C_2$-$C_4$ linear or branched chain alkylene group, and particularly preferably ethylene, trimethylene, or propylene group. When p is an integer of 2 or more, R$^4$ in the respective pairs of brackets (R$^4$ in two or more occurrences) may be identical or different. When R$^4$ in two or more occurrences is different from each other, the structures in the respective pairs of brackets with p may be added (polymerized) in a random form or block form.

In Formula (b-1), p indicates the repetition number of the structure unit in the brackets with p and represents an integer of 1 or more. The repetition number p is typically preferably from 1 to 100, more preferably from 1 to 70, and furthermore preferably from 1 to 30. The amine compound, if having a repetition number p greater than 100, may cause the epoxy-amine adduct according to the present invention to have insufficient heat resistance and may cause the fiber-reinforced composite material to have insufficient heat resistance and/or mechanical properties such as toughness in some uses.

In Formula (b-1), R$^3$ and R$^4$ in each occurrence may be identical or different.

The amine compound (B) is also exemplified by a compound (polyetheramine) represented by Formula (b-2):
[Chem. 9]

(b-2)

In Formula (b-2), s indicates the repetition number of the structural unit in the brackets with s, represents an integer of 1 or more, and is preferably from 1 to 100, more preferably from 1 to 70, and furthermore preferably from 1 to 30. In Formula (b-2), t indicates the number of the structure bonded to R$^6$ and indicated in the brackets with t. The number t represents an integer of 3 or more and is preferably from 3 to 6, more preferably from 3 to 5, and furthermore preferably 3 or 4.

R$^5$ in Formula (b-2) is, in each occurrence independently, selected from a divalent linear, branched chain, or cyclic aliphatic hydrocarbon group; and a divalent group including one or more linear or branched chain aliphatic hydrocarbon groups and one or more cyclic aliphatic hydrocarbon groups linked to each other. The divalent linear, branched chain, or cyclic aliphatic hydrocarbon group is exemplified by the divalent linear, branched chain, or cyclic aliphatic hydrocarbon groups exemplified as R$^2$. R$^6$ represents an organic group having a valency of t and having a carbon atom at each bonding site with the oxygen atom specified in the formula. The organic group as R$^6$ is exemplified by groups as with R$^2$, such as t-valent linear or branched chain aliphatic hydrocarbon groups and t-valent cyclic aliphatic hydrocarbon groups.

The amine compound (B) may also be available as commercial products typically under the trade names of JEFFAMINE D-230, JEFFAMINE D-400, JEFFAMINE D-2000, JEFFAMINE D-4000, JEFFAMINE HK-511, JEFFAMINE ED-600, JEFFAMINE ED-900, JEFFAMINE ED-2003, JEFFAMINE EDR-148, JEFFAMINE EDR-176, JEFFAMINE XTJ-582, JEFFAMINE XTJ-578, JEFFAMINE XTJ-542, JEFFAMINE XTJ-548, JEFFAMINE XTJ-559, JEFFAMINE T-403, JEFFAMINE T-3000, and JEFFAMINE T-5000 (each from Huntsman Corporation).

Epoxy-Amine Adduct Production Method: Reaction between epoxy compound (A) and amine compound (B)

The epoxy-amine adduct according to the present invention may be produced by allowing the epoxy compound (A) and the amine compound (B) to react with each other. More specifically, the alicyclic epoxy groups of the epoxy compound (A) and the amino groups of the amine compound (B), upon reaction with each other, give the epoxy-amine adduct according to the present invention.

Each of different epoxy compounds (A) may be used alone or in combination to produce the epoxy-amine adduct according to the present invention. Likewise, each of different amine compounds (B) may be used alone or in combination.

The reaction (reaction between the epoxy compound (A) and the amine compound (B)) may be allowed to proceed in the presence of, or in the absence of (i.e., without the use of), a solvent. The solvent is not limited, but is preferably one in which the epoxy compound (A) and the amine compound (B) can be dissolved or dispersed uniformly. More specifically, the solvent is exemplified by aliphatic hydrocarbons such as hexane, heptane, and octane; alicyclic hydrocarbons such as cyclohexane; aromatic hydrocarbons such as benzene, toluene, xylenes, and ethylbenzene; halogenated hydrocarbons such as chloroform, dichloromethane, and 1,2-dichloroethane; ethers such as diethyl ether, dimethoxyethane, tetrahydrofuran, and dioxane; ketones such as acetone, methyl ethyl ketone, and methyl isobutyl ketone; esters such as methyl acetate, ethyl acetate, isopropyl acetate, and butyl acetate; amides such as N,N-dimethylformamide and N,N-dimethylacetamide; nitriles such as acetonitrile, propionitrile, and benzonitrile; alcohols such as methanol, ethanol, isopropyl alcohol, and butanol; and dimethyl sulfoxide. Each of different solvents may be used alone or in combination.

The reaction may be allowed to proceed in the presence of, or in the absence of (substantially in the absence of), a catalyst. More specifically, the reaction may be allowed to proceed in the presence of a catalyst when an aromatic amine compound is used as the amine compound (B), where the aromatic amine compound refers to a compound having an amino group substituted on an aromatic ring. In contrast, the reaction is preferably allowed to proceed in the absence of a catalyst when a non-aromatic amine compound is used the amine compound (B), where the non-aromatic amine compound refers to an amine compound other than aromatic amine compounds.

The catalyst is exemplified by, but not limited to, curing accelerators for use in curing of epoxy resins (epoxy compounds) with amine curing agents. Specifically, the catalyst is exemplified by tertiary amines such as lauryldimethylamine, N,N-dimethylcyclohexylamine, N,N-dimethylbenzylamine, N,N-dimethylaniline, (N,N-dimethylaminomethyl)phenol, 2,4,6-tris(N,N-dimethylaminomethyl)phenol, 1,8-diazabicyclo[5.4.0]undecene-7 (DBU), and 1,5-diazabicyclo[4.3.0]nonene-5 (DBN); tertiary amine salts such as carboxylic acid salts, sulfonic acid salts, and inorganic acid salts of the tertiary amines; imidazoles such as 2-methylimidazole, 2-ethylimidazole, 1,2-dimethylimidazole, 2-ethyl-4-methylimidazole, 2-phenylimidazole, 2-phenyl-4-methylimidazole, and 1-benzyl-2-methylimidazole; organic phosphorus compounds such as triphenylphosphine and triphenyl phosphite; onium salts including quaternary ammonium salts such as tetraethylammonium bromide and tetrabutylammonium bromide, quaternary phosphonium salts such as tetrabutylphosphonium decanoate, tetrabutylphosphonium laurate, tetrabutylphosphonium myristate, tetrabutylphosphonium palmitate, a salt between a tetrabutylphosphonium cation and an anion of bicyclo[2.2.1]heptane-2,3-dicarboxylic acid and/or methylbicyclo[2.2.1]heptane-2,3-dicarboxylic acid, and a salt between a tetrabutylphosphonium cation and an anion of 1,2,4,5-cyclohexanetetracarboxylic acid, as well as quaternary arsonium salts, tertiary sulfonium salts, tertiary selenonium salts, secondary iodonium salts, and diazonium salts; strong acid esters such as sulfuric acid esters, sulfonic acid esters, phosphoric acid esters, phosphinic acid esters, and phosphoric acid esters; complexes between a Lewis acid and a base, such as boron trifluoride-aniline complex, boron trifluoride-p-chloroaniline complex, boron trifluoride-ethylamine complex, boron trifluoride-isopropylamine complex, boron trifluoride-benzylamine complex, boron trifluoride-dimethylamine complex, boron trifluoride-diethylamine complex, boron trifluoride-dibutylamine complex, boron trifluoride-piperidine complex, boron trifluoride-dibenzylamine complex, and boron trichloride-dimethyloctylamine complex; and organometallic salts such as tin octanoate, zinc octanoate, dibutyltin dilaurate, and aluminum complex with acetylacetone.

Particularly when the non-aromatic amine compound is used as the amine compound (B), the catalyst may be used in an amount not critical, but preferably less than 1 part by weight (e.g., from 0 to less than 1 part by weight), more preferably less than 0.5 part by weight, and furthermore preferably less than 0.3 part by weight, per 100 parts by weight of the epoxy compound (A). The catalyst, if used in an amount of 1 part by weight or more, may cause a —NH— group formed by the reaction between the epoxy compound (A) and the amine compound (B) to further react with the alicyclic epoxy groups of the epoxy compound (A). This may cause the resulting epoxy-amine adduct to be hardly blended with another component.

When an aromatic amine compound is used as the amine compound (B), the catalyst may be used in an amount not critical, but preferably from 0.1 to 10 parts by weight, more preferably from 0.5 to 8 parts by weight, and furthermore preferably from 1 to 5 parts by weight, per 100 parts by weight of the epoxy compound (A). The catalyst, if used in an amount less than 0.1 part by weight, may fail to help the reaction between the epoxy compound (A) and the amine compound (B) to proceed sufficiently. In contrast, the catalyst, if used in an amount greater than 10 parts by weight, may invite an economical disadvantage.

The ratio of the epoxy compound (A) to the amine compound (B) to be subjected to the reaction is not critical, but is preferably adapted so that the ratio [alicyclic epoxy group/amino group] of the alicyclic epoxy groups of the epoxy compound (A) to the amino groups of the amine compound (B) in the reaction is preferably from 0.05 to 1.00, more preferably from 0.10 to 0.95, and furthermore preferably from 0.15 to 0.90. The reaction, if performed at a ratio [alicyclic epoxy group/amino group] less than 0.05, may cause the amine compound (B) to remain as unreacted in a large amount. In contrast, the reaction, if performed at a ratio [alicyclic epoxy group/amino group] greater than 1.00, may cause the epoxy compound (A) to remain as unreacted.

The reaction may be performed at a temperature (reaction temperature) not critical, but preferably from 30° C. to 250° C., more preferably from 80° C. to 200° C., and furthermore preferably from 120° C. to 180° C. The reaction, if performed at a temperature lower than 30° C., may proceed at a lower reaction rate to cause the epoxy-amine adduct to be produced with lower productivity. In contrast, the reaction, if performed at a temperature higher than 250° C., may cause the epoxy compound (A) and/or the amine compound (B) to decompose and may cause the epoxy-amine adduct to be produced in a lower yield. The reaction temperature may be controlled so as to be always constant (substantially constant) or to be varied stepwise or continuously during the reaction.

The reaction may be performed for a time (reaction time) not critical, but preferably from 0.2 to 20 hours, more preferably from 0.5 to 10 hours, and furthermore preferably from 1 to 5 hours. The reaction, if performed for a time shorter than 0.2 hour, may cause the epoxy-amine adduct to be produced in a lower yield. In contrast, the reaction, if performed for a time longer than 20 hours, may cause the epoxy-amine adduct to be produced with lower productivity.

The reaction may be performed under any pressure, such as under normal atmospheric pressure, under pressure (under a load), or under reduced pressure. The reaction may also be performed in any atmosphere, such as an inert gas (e.g., nitrogen or argon) or air atmosphere.

The reaction may be performed in any system selected from batch, semi-batch, and continuous flow systems without limitation. For example, the reaction, when performed in a batch system, may be performed typically by charging the epoxy compound (A), the amine compound (B), and other optional components such as a solvent according to necessity in a batch reactor; and further heating and/or stirring them according to necessity.

The reaction (reaction between the epoxy compound (A) and the amine compound (B)) gives the epoxy-amine adduct according to the present invention. After the reaction, the epoxy-amine adduct according to the present invention can be separated and purified typically by a known or customary separation means such as filtration, concentration, distillation, extraction, crystallization, recrystallization, or column chromatography, or a separation means as any combination of them.

The epoxy-amine adduct according to the present invention has amino groups (—NH$_2$; unsubstituted amino groups) in a number of 2 or more, preferably from 2 to 10, more preferably from 2 to 4, and furthermore preferably 2 or 3. The epoxy-amine adduct according to the present invention may be substantially devoid of epoxy groups (particularly, alicyclic epoxy groups derived from the epoxy compound (A)).

The amino groups (—NH$_2$; unsubstituted amino groups) in the epoxy-amine adduct according to the present invention may be positioned at any positions not limited, but are generally positioned at molecular chain ends of the epoxy-amine adduct. In particular, the amino groups are generally positioned at both ends of molecular chain of the epoxy-amine adduct when it is a linear epoxy-amine adduct. The positions, however, are not limited thereto.

The epoxy-amine adduct according to the present invention is formed by the reaction between the alicyclic epoxy groups of the epoxy compound (A) and the amino groups (—NH$_2$; unsubstituted amino groups) of the amine compound (B), as described above. The epoxy-amine adduct according to the present invention generally contains a —NH— group or groups remaining in the molecule. This is probably because the —NH— group (substituted amino group) may offer poor reactivity with the alicyclic epoxy groups of the epoxy compound (A), where the —NH— group is formed by the reaction of the alicyclic epoxy groups and the amino groups. The epoxy-amine adduct according to the present invention may contain the —NH— group in a number not critical, but preferably from 1 to 200, more preferably from 1 to 150, and furthermore preferably from 2 to 100 per molecule. The epoxy-amine adduct, if devoid of —NH— groups, may offer lower reactivity, or, in some uses, may fail to effectively contribute to sufficiently better adhesion between the resin and the reinforcing fiber in the fiber-reinforced composite material. The number of the —NH— group in the epoxy-amine adduct can be calculated typically by determining the numbers of the epoxy compound (A) and the amine compound (B) constituting the epoxy-amine adduct based on a molecular weight measured by gel permeation chromatography (GPC) and calibrated with a polystyrene standard.

In contrast, assume that the amine compound (B) is allowed to react typically with a glycidyl-containing epoxy compound. In this case, the resulting compound (epoxy-amine adduct) generally contains substantially no —NH— group. This is because, although the reaction between the glycidyl group and the amino group (unsubstituted amino group) also gives an —NH— group, the —NH— group and the glycidyl group are highly reactive with each other.

The epoxy-amine adduct according to the present invention may have a number-average molecular weight not critical, but preferably from 200 to 40000, more preferably from 300 to 30000, and furthermore preferably from 400 to 20000. The epoxy-amine adduct, if having a number-average molecular weight less than 200, may give rise to functions as an epoxy-amine adduct insufficiently. In contrast, the epoxy-amine adduct, if having a number-average molecular weight greater than 40000, may be hardly blended with another component. The number-average molecular weight of the epoxy-amine adduct may be calculated typically based on a molecular weight measured by gel permeation chromatography and calibrated with a polystyrene standard.

The epoxy-amine adduct according to the present invention may have a glass transition temperature (Tg) not critical, but preferably from −50° C. to 200° C., more preferably from −40° C. to 190° C., and furthermore preferably from −30° C. to 180° C. The epoxy-amine adduct, if having a glass transition temperature Tg lower than −50° C., may cause the fiber-reinforced composite material to have insufficient heat resistance and/or mechanical properties (such as toughness) in some uses. In contrast, the epoxy-amine adduct, if having a glass transition temperature Tg higher than 200° C., may be hardly blended with another component. The glass transition temperature of the epoxy-amine adduct can be measured typically by differential scanning calorimetry (DSC) and/or dynamic viscoelastic measurement.

In an embodiment, the epoxy-amine adduct according to the present invention may be formed from the compound represented by Formula (a) as the epoxy compound (A); and the compound represented by Formula (b) in which r is 2 as the amine compound (B). Particularly in this embodiment, the epoxy-amine adduct is represented by Formula (I):

[Chem. 10]

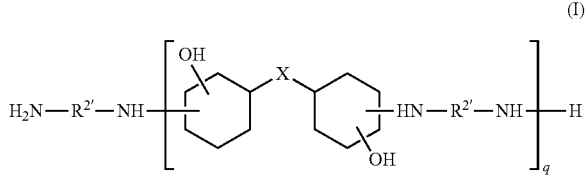

In Formula (I), R$^{2'}$ represents, in each occurrence independently, a divalent organic group (organic residue) having a carbon atom at each bonding site with the nitrogen atom specified in the formula. R$^{2'}$ is exemplified by the divalent groups exemplified as R$^2$ in Formula (b).

X in Formula (I) is, in each occurrence independently, selected from a single bond and a linkage group (divalent group having at least one atom) and is exemplified as with X in Formula (a). When q is an integer of 2 or more, X in two or more occurrences may be identical or different.

In Formula (I), q indicates the repetition number of the structural unit in the brackets with q and represents an integer of 1 or more. Though not critical, the repetition number q is preferably from 1 to 200, more preferably from 2 to 150, and furthermore preferably from 2 to 100. The epoxy-amine adduct, if having a repetition number q greater than 200, may be hardly blended with another component. The repetition number q in Formula (I) can be controlled typically by adjusting the ratio of the epoxy compound (A) to the amine compound (B) to be subjected to the reaction, and the reaction conditions.

Assume that, of carbon atoms constituting each cyclohexane ring in Formula (I), a carbon atom to which X is bonded is designated as a "1-position" carbon atom. In this case, the nitrogen atom (—NH—) bonded to the cyclohexane ring in Formula (I) is positioned at the 3-position carbon atom or at the 4-position carbon atom. When the nitrogen atom is located on the 3-position carbon atom, the hydroxyl group (—OH) bonded to the cyclohexane ring in Formula (I) is positioned at the 4-position carbon atom.

When the nitrogen atom is located on the 4-position carbon atom of the cyclohexane ring, the hydroxyl group (—OH) bonded to the cyclohexane ring in Formula (I) is positioned at the 3-position carbon atom. The bonding positions of the nitrogen atoms (or the bonding positions of the hydroxyl groups) in the two or more cyclohexane rings may be identical or different. When carbon atoms constituting the cyclohexane rings in Formula (I) are designated with the locants, Formula (I) is expressed as follows:

[Chem. 11]

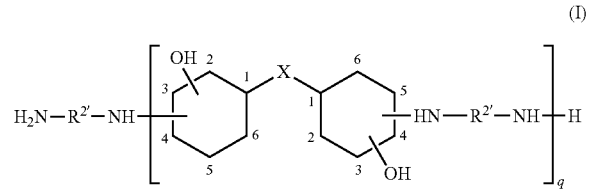

(I)

The epoxy-amine adduct according to the present invention, when represented by Formula (I), may be a mixture of two or more epoxy-amine adducts having different repetition numbers q.

Of the epoxy-amine adducts represented by Formula (I), epoxy-amine adducts represented by Formula (I-1) are preferred, and epoxy-amine adducts represented by Formula (I-2) are more preferred. X and q in Formula (I-1) and q in Formula (I-2) are as with X and q in Formula (I), respectively. In Formulae (I-1) and (I-2), p represents, in each occurrence independently, an integer of 1 or more and is as with p in Formula (b-1). $R^3$ and $R^4$ in Formulae (I-1) and (I-2) are, in each occurrence independently, selected from a divalent linear, branched chain, or cyclic aliphatic hydrocarbon group and a divalent group including one or more linear or branched chain aliphatic hydrocarbon groups and one or more cyclic aliphatic hydrocarbon groups linked to each other. $R^3$ and $R^4$ herein are as with $R^3$ and $R^4$ in Formula (b-1). When p is an integer of 2 or more, corresponding $R^4$ in plural occurrences may be identical or different. When $R^4$ in two or more occurrences is different from each other, the structures in the respective pairs of brackets with p may be added (polymerized) in a random form or block form. $R^3$ and $R^4$ may be identical groups or different groups in each occurrence.

[Chem. 12]

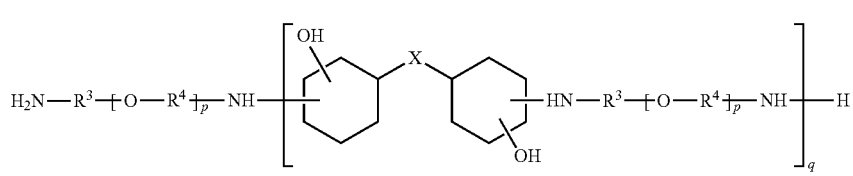

(I-1)

[Chem. 13]

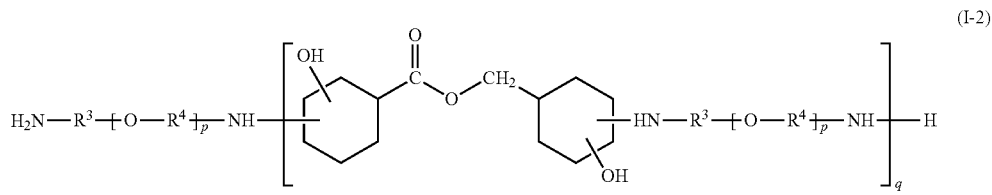

(I-2)

Resin Composition

The epoxy-amine adduct according to the present invention, when blended (mixed) with a known or customary resin, gives a resin composition. This is also referred to as a "resin composition according to the present invention." The resin is not limited, but exemplified by thermoplastic resins including polyolefins (e.g., polyethylenes, polypropylenes, and polybutadiene), vinyl polymers (e.g., acrylic resins and polystyrenes), polyamides (e.g., nylon 6, nylon 66, nylon 11, nylon 12, nylon 610, nylon 612, nylon 61, nylon 6T, and nylon 9T), polyesters (e.g., poly(ethylene terephthalate)s and poly(butylene terephthalate) s), poly (vinyl chloride)s, poly(vinylidene chloride)s, polycarbonates, polyacetals, poly(phenylene oxide)s, poly(phenylene sulfide)s, polyethersulfones, poly(ether ether ketone)s; and curable resins (curable compounds) such as epoxy resins, unsaturated polyesters, vinyl ester resins, allyl resins (e.g., diallyl phthalate resins), phenolic resins, polyimides, cyanate resins, maleimide resins, urea resins, melamine resins, and silicone resins. Such curable resins include thermosetting (heat-curable) resins (thermosetting compounds) and photo-curable resins (photo-curable compounds). It should be noted, however, the "resin" does not include the epoxy-amine adducts according to the present invention. The resin composition according to the present invention may employ each of different resins alone or in combination.

Among them, a resin composition using a thermoplastic resin as the resin, namely, a resin composition (thermoplastic resin composition) including at least the epoxy-amine adduct according to the present invention and a thermoplastic resin can be advantageously molded (shaped) in a shorter time than curable resin compositions (e.g., thermosetting resin compositions and photo-curable resin compositions).

For this reason, the resin composition including at least the epoxy-amine adduct according to the present invention and a thermoplastic resin is particularly preferably usable in uses requiring a shorter molding time, such as automobile parts uses.

The resin composition according to the present invention may contain the resin in a content (blending amount) not critical, but preferably from 0.1 to 99.9 percent by weight, more preferably from 1 to 99 percent by weight, and furthermore preferably from 2 to 98 percent by weight, based on the total amount (100 percent by weight) of the resin composition. The resin composition, if containing the resin in a content less than 0.1 percent by weight, may cause the resulting fiber-reinforced composite material to have insufficient heat resistance and/or mechanical properties (such as toughness) in some uses. In contrast, the resin composition, if containing the resin in a content greater than 99.9 percent by weight, may cause the fiber-reinforced composite material to suffer from insufficient adhesion between the resin and the reinforcing fiber in some uses.

The resin composition according to the present invention may employ each of different epoxy-amine adducts according to the present invention alone or in combination.

The resin composition according to the present invention may contain the epoxy-amine adduct according to the present invention in a content (blending amount) not critical, but preferably from 0.1 to 200 parts by weight, more preferably from 1 to 100 parts by weight, and furthermore preferably from 2 to 50 parts by weight, per 100 parts by weight of the resin. The resin composition, if containing the epoxy-amine adduct according to the present invention in a content less than 0.1 part by weight, may cause the fiber-reinforced composite material to suffer from insufficient adhesion between the resin and the reinforcing fiber in some uses. In contrast, the resin composition, if containing the epoxy-amine adduct according to the present invention in a content greater than 200 parts by weight, may cause the fiber-reinforced composite material to have insufficient heat resistance and/or mechanical properties (such as toughness) in some uses.

The resin composition according to the present invention may contain one or more customary additives in addition to the resin and the epoxy-amine adduct according to the present invention. Such additives are exemplified by polymerization initiators (e.g., thermal initiators and photoinitiators), curing agents, curing accelerators, antifoaming agents, leveling agents, coupling agents (e.g., silane coupling agents), surfactants, inorganic fillers (e.g., silica and alumina), flame retardants, colorants, antioxidants, ultraviolet absorbers, ion adsorbents, pigments, phosphors, and releasing agents.

The resin composition according to the present invention has only to contain at least both the epoxy-amine adduct according to the present invention and the resin, and its production method (preparation method) is not limited. Specifically, the resin composition may be prepared typically by mixing and stirring predetermined proportions of components to form the resin composition. The mixing and stirring of the individual components may employ a known apparatus such as a planetary centrifugal mixer, planetary mixer, kneader, or dissolver.

The epoxy-amine adduct in the resin composition according to the present invention offers high reactivity and contributes to better adhesion between a reinforcing fiber and a resin in a fiber-reinforced composite material, where the fiber-reinforced composite material is a composite material between the reinforcing fiber (e.g., a carbon fiber) and the resin. The resin composition is therefore preferably usable particularly as a resin composition to form a fiber-reinforced composite material (resin composition for a fiber-reinforced composite material). Specifically, the fiber-reinforced composite material may be formed from a prepreg that is obtained by impregnating or coating a reinforcing fiber with the resin composition according to the present invention. More specifically, in an embodiment, the resin composition according to the present invention is a resin composition containing at least the epoxy-amine adduct according to the present invention and a thermoplastic resin. In this embodiment, the fiber-reinforced composite material may be obtained by impregnating or coating the reinforcing fiber with the resin composition to give a prepreg (thermoplastic prepreg), and further molding or shaping the prepreg, where the resin composition is melted or dissolved in an appropriate solvent upon the impregnation or coating. In contrast, in another embodiment, the resin composition according to the present invention is a resin composition containing at least the epoxy-amine adduct according to the present invention and a curable resin. In this embodiment, the fiber-reinforced composite material may be prepared by impregnating or coating the reinforcing fiber with the resin composition to give a prepreg (curable prepreg); further curing the curable resin in the prepreg and shaping the prepreg. Among them, the thermoplastic prepreg is preferably usable in uses requiring a shorter molding time, such as automobile parts uses.

The reinforcing fiber usable herein may be any of known or customary reinforcing fibers not limited, but is exemplified by carbon fibers, glass fibers, aramid fibers, boron fibers, graphite fibers, silicon carbide fibers, high-strength polyethylene fibers, tungsten carbide fibers, and poly-p-phenylenebenzoxazole fibers (PBO fibers). The carbon fibers are exemplified by polyacrylonitrile (PAN) carbon fibers, pitch-based carbon fibers, and vapor-grown carbon fibers. Among them, carbon fibers, glass fibers, and aramid fibers are preferred from the viewpoint of mechanical properties (such as toughness). Each of different reinforcing fibers may be used alone or in combination.

The reinforcing fiber may be one subjected to a known or customary surface treatment such as coupling, oxidation, and/or coating treatment.

The reinforcing fiber may be in any form not limited and may be in the form of a filament (continuous fiber), a tow, a unidirectional material including tows unidirectionally aligned, a woven fabric, and a nonwoven fabric. Such woven fabrics of reinforcing fibers are exemplified by plain fabrics; twill fabrics; satin fabrics; and stitching sheets that are typified by non-crimp fabrics and produced by preparing a sheet including unidirectionally aligned fiber bundles or a sheet including such fiber bundles laminated with varying lamination angles, and stitching the sheet in order to create integrality of the fabric.

The prepreg according to the present invention (thermoplastic prepreg or curable prepreg) may contain the reinforcing fiber in a content not critical, where the content is adjustable as needed.

In an embodiment, the prepreg according to the present invention is a curable prepreg. In this embodiment, the prepreg may be one prepared by impregnating or coating the reinforcing fiber with the resin composition according to the present invention; and further curing part of curable resin(s) in the resin composition (namely, semi-curing the curable resin(s)). The semi-curing may be performed typically by the application of heat and/or an active energy ray.

The reinforcing fiber may be impregnated or coated with the resin composition according to the present invention by any process not limited, which may be selected from impregnating or coating processes in known or customary prepreg production methods.

The fiber-reinforced composite material according to the present invention is formed from the prepreg according to the present invention, as described above. The process to produce the composite material is not limited, but is exemplified by known or customary processes such as hand lay-up, pre-impregnation, RTM, pultrusion, filament winding, spray-up, or pultrusion molding process.

The fiber-reinforced composite material according to the present invention is usable as materials for various structures and preferably usable as materials for structures including aircraft structures such as fuselages, main planes, tail assemblies, rotor blades, fairings, cowlings, and doors; spacecraft structures such as motor cases and main planes; artificial satellite body structures; automobile parts such as chassis; railway vehicle body structures; bicycle body structures; ship body structures; wind turbine blades; pressure vessels; fishing rods; tennis rackets; golf club shafts; robot arms; and cables (e.g., cable cores).

Sizing Agent

The epoxy-amine adduct according to the present invention offers high reactivity with functional groups (such as hydroxyl, carboxyl, and epoxy groups) present in the surface of the reinforcing fiber and effectively contributes to better adhesion between the resin and the reinforcing fiber in the fiber-reinforced composite material, as described above. The epoxy-amine adduct is also preferably usable as a sizing agent, particularly as a sizing agent for carbon fibers. The "sizing agent" refers to a treatment agent to be applied to a reinforcing fiber so as to help the reinforcing fiber to have better handleability in a production process thereof, or in a high-order processing process such as textile treatment process, pre-impregnation process, or another molding or shaping process. The sizing agent is also called a binder. A sizing agent containing the epoxy-amine adduct according to the present invention is herein also referred to as a "sizing agent according to the present invention."

The sizing agent according to the present invention has only to essentially contain the epoxy-amine adduct according to the present invention. The sizing agent may contain a solvent and/or other optional additives in addition to the epoxy-amine adduct according to the present invention, or may be composed of the epoxy-amine adduct according to the present invention alone (i.e., the epoxy-amine adduct according to the present invention itself).

The solvent which the sizing agent according to the present invention may contain is not limited, but is exemplified by water; aliphatic hydrocarbons such as hexane, heptane, and octane; alicyclic hydrocarbons such as cyclohexane; aromatic hydrocarbons such as benzene, toluene, xylenes, and ethylbenzene; halogenated hydrocarbons such as chloroform, dichloromethane, and 1,2-dichloroethane; ethers such as diethyl ether, dimethoxyethane, tetrahydrofuran, and dioxane; ketones such as acetone, methyl ethyl ketone, and methyl isobutyl ketone; esters such as methyl acetate, ethyl acetate, isopropyl acetate, and butyl acetate; amides such as N,N-dimethylformamide and N,N-dimethylacetamide; nitriles such as acetonitrile, propionitrile, and benzonitrile; alcohols such as methanol, ethanol, isopropyl alcohol, and butanol; and dimethyl sulfoxide. Among them, water and alcohols are preferred, and water is particularly preferred for small load on the environment and working atmosphere. Specifically, the sizing agent according to the present invention may be a solution or dispersion of the epoxy-amine adduct according to the present invention in water and/or an alcohol, of which an aqueous solution or aqueous dispersion is preferred. Each of different solvents may be used alone or in combination.

The sizing agent according to the present invention may further contain any of various additives. The additives are exemplified by lubricants such as fatty acids, amides, and esters; and coupling agents such as silane coupling agents and titanium coupling agents.

Sizing-agent-coated Carbon Fiber

The sizing agent according to the present invention, when applied to a carbon fiber, gives a sizing-agent-coated carbon fiber. This is also referred to as a "sizing-agent-coated carbon fiber according to the present invention."

A process to apply the sizing agent according to the present invention to the carbon fiber is not limited, but is exemplified by known or customary processes such as a process of immersing the carbon fiber with the sizing agent according to the present invention; a process of bringing the carbon fiber into contact with the sizing agent according to the present invention on a roller; and a process of atomizing the sizing agent according to the present invention and spraying the atomized agent to the carbon fiber. The sizing agent according to the present invention may be applied to the entire surface or part of the surface of the carbon fiber. The coating thickness and mass of coating are adjustable as needed and are not critical.

The carbon fiber after the application of the sizing agent according to the present invention may be subjected to a heat treatment according to necessity. The heat treatment conditions are not critical, but a heating temperature is preferably from 40° C. to 300° C. and more preferably from 60° C. to 250° C. A heating time is adjustable as needed according to the heating temperature, is not critical, but is preferably from 1 second to 60 minutes and more preferably from 5 seconds to 10 minutes. The heating temperature in the heat treatment may be kept constant, or may be varied continuously or stepwise. The heat treatment may be performed continuously in one step or intermittently in two or more steps. The heat treatment is generally performed so as to accelerate the impregnation with the sizing agent and to evaporate the solvent to thereby dry the resulting article. The heat treatment may be performed by a known or customary process such as heating in a hot-air oven.

The sizing-agent-coated carbon fiber according to the present invention may be one prepared by applying the sizing agent according to the present invention to the carbon fiber; subjecting the resulting article to a heat treatment; and further coating the article typically with the thermoplastic resin and/or the curable compound (curable resin). This may help the sizing-agent-coated carbon fiber to have reduced tack and to offer better handleability in some types of the thermoplastic resins and the curable resins. The coating may be performed by any process not critical, and can be performed by the procedure to apply the sizing agent according to the present invention to the carbon fiber. The coating may be performed on the entire surface or part of the surface of the sizing-agent-coated carbon fiber. The coating thickness and the mass of coating are also adjustable as needed and are not critical.

The sizing-agent-coated carbon fiber according to the present invention is coated with the epoxy-amine adduct according to the present invention and thereby offers excellent adhesion to a resin. The sizing agent according to the present invention also has excellent functions as a regular sizing agent, such as the functions of binding the carbon fiber and of imparting flexibility to the carbon fiber. The sizing-agent-coated carbon fiber according to the present invention therefore offers good handleability and excellent workability in higher-order processing.

The sizing-agent-coated carbon fiber according to the present invention has the characteristic properties as mentioned above. A fiber-reinforced composite material including the sizing-agent-coated carbon fiber; and a matrix resin therefore has excellent heat resistance and mechanical strengths and is produced with high productivity. The matrix resin is exemplified by the thermoplastic resins; and cured products (cured resins) of the curable compounds (curable resins). The fiber-reinforced composite material may be produced by any of known or customary methods such as the production method of the fiber-reinforced composite material. The fiber-reinforced composite material is preferably usable as materials for the various structures.

EXAMPLES

The present invention will be illustrated in further detail with reference to several examples below. It should be noted, however, that the examples are by no means intended to limit the scope of the invention.

Example 1

As an epoxy compound (A) and an amine compound (B), there were used 3,4-epoxycyclohexylmethyl (3,4-epoxy) cyclohexanecarboxylate [trade name CELLOXIDE 2021P, supplied by Daicel Corporation] and an amine-terminated polypropylene glycol [trade name JEFFAMINE D-230, supplied by Huntsman Corporation], respectively.

As indicated in Table 1, 30.0 parts by weight of the epoxy compound (A) and 35.9 parts by weight of the amine compound (B) were mixed, then allowed to react with each other with stirring at 160° C. for 2 hours, and yielded an epoxy-amine adduct (amine adduct).

Figure 3:
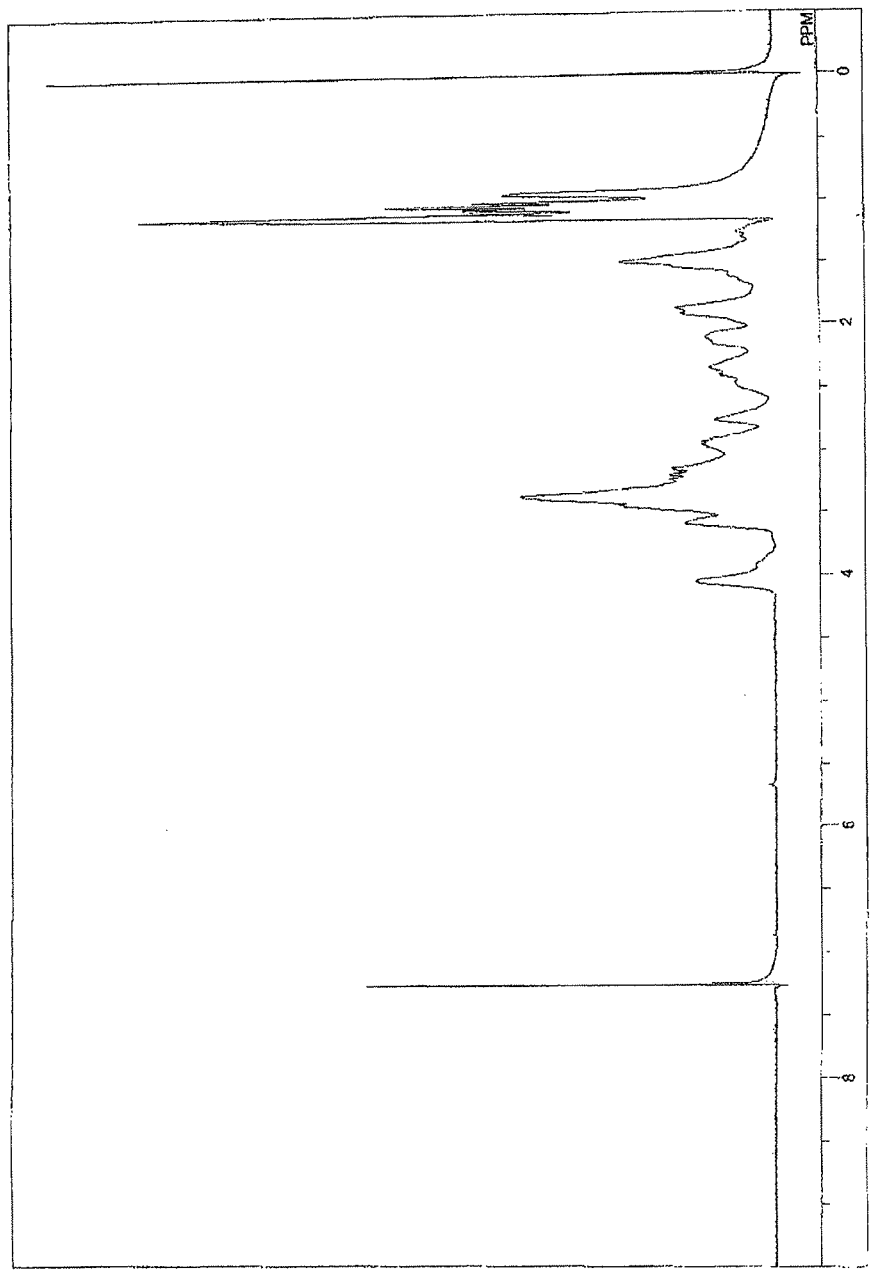
FIG. 3 depicts a ¹H-NMR spectrum chart of an epoxy-amine adduct obtained in Example 1.

Table 1 indicates properties (evaluation results) of the obtained epoxy-amine adduct. FIG. 3 depicts the $^1$H-NMR spectrum chart of the obtained epoxy-amine adduct. When melted and mixed with a polycarbonate using the LABO PLASTOMILL, the obtained epoxy-amine adduct was found to give a press-formable resin composition.

Example 2

As an epoxy compound (A) and an amine compound (B), there were used 3,4-epoxycyclohexylmethyl (3,4-epoxy) cyclohexanecarboxylate [trade name CELLOXIDE 2021P, supplied by Daicel Corporation] and an amine-terminated polypropylene glycol [trade name JEFFAMINE D-230, supplied by Huntsman Corporation], respectively.

As is indicated in Table 1, 20.0 parts by weight of the epoxy compound (A) and 34.6 parts by weight of the amine compound (B) were mixed with each other, then allowed to react with each other with stirring at 160° C. for 2 hours, and yielded an epoxy-amine adduct. The obtained epoxy-amine adduct was soluble in water.

Figure 4:
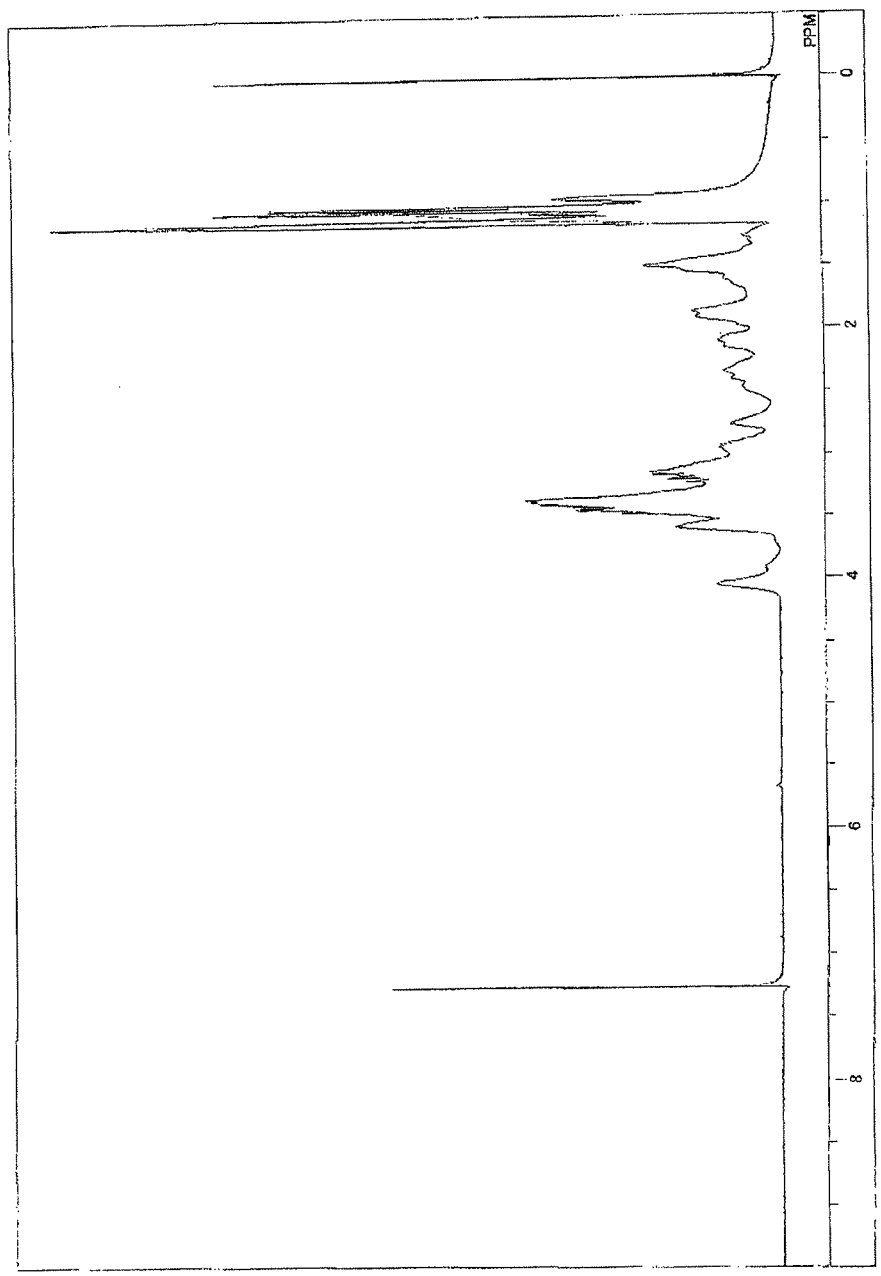
FIG. 4 depicts a ¹H-NMR spectrum chart of an epoxy-amine adduct obtained in Example 2.

Table 1 indicates properties (evaluation results) of the obtained epoxy-amine adduct. FIG. 4 depicts the $^1$H-NMR spectrum chart of the obtained epoxy-amine adduct. When melted and mixed with a polycarbonate using the LABO PLASTOMILL, the obtained epoxy-amine adduct was found to give a press-formable resin composition.

Comparative Example 1

A bisphenol-A epoxy resin [trade name EPOTOHTO YD128, supplied by Nippon Steel Chemical Co., Ltd.] (30.0 parts by weight) and an amine-terminated polypropylene glycol [trade name JEFFAMINE D-230, supplied by Huntsman Corporation] (41.3 parts by weight) were mixed, then allowed to react with each other by stirring at 160° C. for 2 hours, and thereby yielded a resin having no thermoplasticity.

Evaluations

The epoxy-amine adducts obtained in the examples were subjected to evaluations as follows.

(1) Glass Transition Temperature

The glass transition temperatures (Tg) of the epoxy-amine adducts obtained in the examples were measured with a differential scanning calorimeter (DSC) [supplied by Seiko Instruments Inc.]. The measurements were performed at a rate of temperature rise of 10° C./min, at measurement temperatures of from −50° C. to 250° C. with two scans. The glass transition temperatures were determined based on a DSC curve obtained in the second scan. The results are indicated in Table 1.

(2) Viscosity

Viscosities of the epoxy-amine adducts obtained in the examples at 70° C. were measured with an E-type viscometer (cone-and-plate viscometer) [TV-22, supplied by Toki Sangyo Co., Ltd.] at a measurement temperature of 70° C. The results are indicated in Table 1.

For the epoxy-amine adduct obtained in Example 2, the viscosities at 25° C. and at 45° C. were also measured by the same procedure. The results are indicated in Table 1.

(3) Molecular Weight

An eluting solvent was prepared by adding lithium bromide to dimethylformamide (DMF) to a molarity of 30 mM. The epoxy-amine adduct obtained in Example 1 was dissolved in the eluting solvent, filtrated through a 0.45-μm membrane filter to give a filtrate, and the filtrate was used as a molecular weight measurement sample. The measurement sample was subjected to measurements of the weight-average molecular weight (Mw), number-average molecular weight (Mn), peak-top molecular weight (Mp), and molecular weight distribution (Mw/Mn) of the epoxy-amine adduct. The results are indicated in Table 1. The molecular weights (Mw, Mn, and Mp) were obtained as values calibrated with a polystyrene standard.

TABLE 1

| | | | | Example 1 | Example 2 | Comparative Example 1 |
|---|---|---|---|---|---|---|
| Synthesis | Raw materials | CELLOXIDE 2021P | [part by weight] | 30.0 | 20.0 | — |
| | | JEFFAMINE D-230 | [part by weight] | 35.9 | 34.6 | 41.3 |
| | | EPOTOHTO YD-128 | [part by weight] | — | — | 30.0 |
| | Epoxy-amine adduct synthesis conditions (raw material reaction conditions) | | | 160° C., 2 hrs | 160° C., 2 hrs | 160° C., 2 hrs |
| Properties | Glass transition temperature | | [° C.] | 5.6 | −21.3 | — |
| | Viscosity | 70° C. | [mPa · s] | 13970 | 497 | — |
| | | 45° C. | [mPa · s] | — | 4942 | — |
| | | 25° C. | [mPa · s] | — | 47880 | — |

TABLE 1-continued

|  |  | Example 1 | Example 2 | Comparative Example 1 |
|---|---|---|---|---|
| Molecular weights | Mn | 790 | — | — |
|  | Mw | 2700 | — | — |
|  | Mp | 1910 | — | — |
|  | Mw/Mn | 3.4 | — | — |

As is demonstrated in Table 1, the epoxy-amine adducts obtained in the examples had low glass transition temperatures and offered thermoplasticity. They became liquid at highest at 70° C. and could be mixed with another component such as a thermoplastic resin. The epoxy-amine adducts obtained in the examples had —NH— groups in the molecule, thereby had high reactivity, and could contribute to better adhesion between the resin and the reinforcing fiber (particularly, the carbon fiber).

In contrast, the resin obtained in the comparative example offered no thermoplasticity and was hardly blended with another component.

Example 3

The epoxy-amine adduct obtained in Example 1 was uniformly dissolved in a mixture of ethanol and water (containing 6% of ethanol) and yielded a solution, as a sizing agent, containing about 2 percent by weight of the epoxy-amine adduct. Specifically, the epoxy-amine adduct obtained in Example 1 was soluble in the mixture. The sizing agent was applied to a surface-treated carbon fiber by immersion and subsequently heat-treated at a temperature of 210° C. for 90 seconds. The resulting article was then immersed in a bisphenol-A epoxy resin [trade name EPO-TOHTO YD128, supplied by Nippon Steel Chemical Co., Ltd.], treated at 100° C. for 30 minutes, and yielded a tackless carbon fiber bundle (sizing-agent-coated carbon fiber bundle).

The components used in the examples and comparative example are as follows.

Epoxy Compound

CELLOXIDE 2021P: 3,4-Epoxycyclohexylmethyl (3,4-epoxy)cyclohexanecarboxylate, supplied by Daicel Corporation EPOTOHTO YD-128: Bisphenol-A epoxy resin, supplied by Nippon Steel Chemical Co., Ltd.

Amine Compound

JEFFAMINE D-230: Amine-terminated polypropylene glycol, supplied by Huntsman Corporation

INDUSTRIAL APPLICABILITY

The epoxy-amine adduct according to the present invention offers high reactivity with a functional group (e.g., hydroxyl, carboxyl, or epoxy group) present in the surface of a reinforcing fiber and effectively contributes to better adhesion between a resin and the reinforcing fiber in a fiber-reinforced composite material. The epoxy-amine adduct is preferably usable as a sizing agent (particularly, sizing agent for carbon fibers). A resin composition containing the epoxy-amine adduct according to the present invention is preferably usable particularly as a resin composition to form a fiber-reinforced composite material (resin composition for a fiber-reinforced composite material). The fiber-reinforced composite material according to the present invention is usable as materials for various structures and is preferably usable as materials for structures including aircraft structures such as fuselages, main planes, tail assemblies, rotor blades, fairings, cowlings, and doors; spacecraft structures such as motor cases and main planes; artificial satellite structures such as body structures; automobile parts such as automobile chassis; railway vehicle body structures; bicycle body structures; ship body structures; wind turbine blades; pressure vessels; fishing rods; tennis rackets; golf club shafts; robot arms; and cables (e.g., cable cores).

The invention claimed is:

1. An epoxy-amine adduct
obtained by a reaction of an epoxy compound (A) having two or more alicyclic epoxy groups per molecule with an amine compound (B) represented by Formula (b1) and an amine compound (B) represented by Formula (b2):

$$R^{21}(NH_2)_{r1} \quad (b1)$$

wherein $R^{21}$ represents a divalent group comprising two or more divalent linear or branched chain aliphatic hydrocarbon groups bonded to each other via a heteroatom-containing linkage group; and r1 represents 2;

$$R^{22}(NH_2)_{r2} \quad (b2)$$

wherein $R^{22}$ represents a divalent group comprising a divalent linear or branched chain aliphatic hydrocarbon group and a divalent cyclic aliphatic hydrocarbon group directly bonded to each other; and r2 represents 2.

2. The epoxy-amine adduct according to claim 1, wherein the epoxy compound (A) comprises a compound represented by Formula (a):

[Chem. 3]

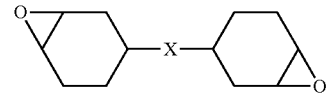

(a)

wherein X is selected from a single bond and a divalent group comprising at least one atom.

3. A resin composition comprising:
the epoxy-amine adduct of claim 1; and
a thermoplastic resin.

4. The resin composition according to claim 3, as a resin composition for a fiber-reinforced composite material.

5. A prepreg comprising:
the resin composition of claim 4; and
a reinforcing fiber impregnated or coated with the resin composition.

6. A fiber-reinforced composite material formed from the prepreg of claim 5.

7. A sizing agent comprising the epoxy-amine adduct of claim 1.

8. A sizing-agent-coated carbon fiber comprising:
a carbon fiber; and
the sizing agent of claim 7 applied to the carbon fiber.

9. A fiber-reinforced composite material comprising:
the sizing-agent-coated carbon fiber of claim 8; and
one selected from the group consisting of:
  a thermoplastic resin; and
  a cured product of a curable compound.

* * * * *